US011937926B2

(12) United States Patent
Canty et al.

(10) Patent No.: US 11,937,926 B2
(45) Date of Patent: Mar. 26, 2024

(54) METHOD FOR OPTIMIZING TREATMENT OF INFECTED METALLIC IMPLANTS BY MEASURING CHARGE TRANSFER

(71) Applicant: Garwood Medical Devices, LLC, Buffalo, NY (US)

(72) Inventors: Mary K. Canty, Tonawanda, NY (US); Jackson G. Hobble, Buffalo, NY (US)

(73) Assignee: GARWOOD MEDICAL DEVICES, LLC, Buffalo, NY (US)

( * ) Notice: Subject to any disclaimer, the term of this patent is extended or adjusted under 35 U.S.C. 154(b) by 0 days.

(21) Appl. No.: 18/013,747

(22) PCT Filed: Jun. 29, 2021

(86) PCT No.: PCT/US2021/039529
§ 371 (c)(1),
(2) Date: Dec. 29, 2022

(87) PCT Pub. No.: WO2022/006056
PCT Pub. Date: Jan. 6, 2022

(65) Prior Publication Data
US 2023/0255526 A1    Aug. 17, 2023

Related U.S. Application Data

(60) Provisional application No. 63/047,308, filed on Jul. 2, 2020.

(51) Int. Cl.
*A61L 2/03* (2006.01)
*A61B 5/1468* (2006.01)
(Continued)

(52) U.S. Cl.
CPC ............. *A61B 5/1468* (2013.01); *A61L 2/03* (2013.01); *A61N 1/18* (2013.01); *A61L 27/28* (2013.01)

(58) Field of Classification Search
CPC ......... A61B 5/1468; A61L 2/03; A61L 27/28; A61L 2202/14; A61L 2202/21; A61N 1/18; A61N 1/205
See application file for complete search history.

(56) References Cited

U.S. PATENT DOCUMENTS 10,406,211 B2    9/2019  Newman et al.
2013/0319869 A1  12/2013 Turner
(Continued)

FOREIGN PATENT DOCUMENTS

WO    2020/247422 A1   12/2020
WO    2022006056  A1    1/2022

OTHER PUBLICATIONS

Canadian Intellectual Property Office; First Examination Search Report; Application No. 3,183,538 dated Jan. 20, 2023; 4 pages.
(Continued)

*Primary Examiner* — Sean E Conley
*Assistant Examiner* — Brendan A Hensel
(74) *Attorney, Agent, or Firm* — Barclay Damon LLP (57) ABSTRACT

A method and related system for treating a metallic surface in order to eradicate bacteria on the metallic surface using at least three electrodes and in which the metallic surface is one of the electrodes and in which a stimulation voltage is applied to the metallic surface and an accumulated charge is measured. The accumulated charge is compared to a threshold level wherein the stimulation voltage is maintained until the accumulated charge exceeds the threshold level. In at least one version, the metallic surface is that of a surgical implant.

16 Claims, 5 Drawing Sheets

(51) Int. Cl.
   *A61L 27/28*   (2006.01)
   *A61N 1/18*   (2006.01)

(56) References Cited

U.S. PATENT DOCUMENTS

| | | | |
|---|---|---|---|
| 2014/0378964 A1* | 12/2014 | Pearson | A61B 18/1477 |
| | | | 606/41 |
| 2016/0000947 A1 | 1/2016 | Brodbeck | |
| 2017/0056536 A1 | 3/2017 | Hallab et al. | |
| 2017/0304501 A1 | 10/2017 | Bunge et al. | |
| 2018/0207301 A1 | 7/2018 | Beyenal et al. | |
| 2019/0105414 A1* | 4/2019 | Ehrensberger | A61F 2/30 |

OTHER PUBLICATIONS

U.S. International Searching Authority; International Search Report and Written Opinion; dated Oct. 14, 2021; Date of Completion: Sep. 15, 2021; 12 pages.

U.S. International Preliminary Examining Authority; International Preliminary Report on Patentability: dated Mar. 22, 2022; Date of Completion: Mar. 15, 2022; 18 pages.

Australian Intellectual Property Office; First Examination Search Report; Application No. 2021300277 dated Feb. 8, 2023; 2 pages.

European Patent Office; Extended European Search Report; Date of Completion of Search: Nov. 14, 2023; dated Dec. 1, 2023; 7 pages.

\* cited by examiner

Comparison of time-based treatment vs. charge-based treatments

FIG. 3

Cumulative charge transfer compared to duration of treatment at -2.0V vs. Ag/AgCl Relationship Between charge transfer and viable colony forming units (CFU) of 6 clinically relevant strains of bacteria. Results shown represent remaining biofilm associated bacteria.

FIG. 4

Relationship between charge transfer and viable colony forming units (CFU) of 6 clinically relevant strains of bacteria. Results shown represent remaining planktonic bacteria.

FIG. 5

METHOD FOR OPTIMIZING TREATMENT OF INFECTED METALLIC IMPLANTS BY MEASURING CHARGE TRANSFER

CROSS-REFERENCE TO RELATED APPLICATIONS

This application is a national stage application filed pursuant to 35 U.S.C. § 371 of International Application No. PCT/US2021/039529, which was filed on Jun. 29, 2021 and claims priority to U.S. Ser. No. 63/047,308 filed on Jul. 2, 2020. The entire contents of this PCT application is hereby incorporated by reference.

TECHNICAL FIELD

This application is generally directed to the field of treatment systems that are used to disrupt or eradicate bacteria from metallic surfaces. More specifically, this application is directed to a system and related method or technique for reliably controlling the treatment of infected metal implanted devices, based on measured charge transfer.

BACKGROUND

Implants are used in patients with many different injuries or medical problems. For example, various surgically implanted orthopedic devices such as knee, hip and shoulder joint replacements are routine. Similarly, implants may be used for any individual that needs to replace a tooth in a dental procedure. These implants are typically made from metals, such as titanium, cobalt chrome, or stainless steel. A potential problem with metal implants in general is that these devices tend to allow for the growth of bacteria on the surface, increasing the patient's risk for infection. As bacteria colonize upon foreign surfaces such as metal, biofilms are formed. Biofilms are protective extracellular matrix materials that encapsulate bacterial colonies onto a surface and protect the colonies. Biofilms can be 500-5000 times more resistant to antibiotics than common planktonic bacteria because the antibiotics cannot penetrate the biofilm.

Implant associated infections are a devastating outcome of medical intervention that has led to increased patient morbidity and rising costs to the health care system. Unfortunately, the current standard of care often requires removal of the infected implant, long term antibiotic treatment, and eventual secondary replacement. More recent developments in the field provide for a treatment system, as described in U.S. Pat. No. 9,616,142. The described treatment system can be performed on the patient without requiring removal of the implanted device. More specifically and according to this technique, an electrochemical cell is created using two or more and preferably three electrodes each coupled to a device, such as a potentiostat, which is capable of delivering a stimulation voltage. A counter electrode and a stable reference electrode are each attached to the patient along with a working electrode, the latter being the metal implant, forming an electrochemically based circuit. The applied stimulation voltage is sufficient to disrupt and eradicate the biofilm layer.

Unfortunately, it is unknown how long to treat the patient using electrical stimulation such as described above before the infection actually clears. Due to differences in patient physiology, hydration, fat content, and other patient specific variables, each patient receives different levels of applied current while maintaining a constant voltage. Current methods do not allow for a scientific and mathematically backed way of determining exactly how much treatment is required to eradicate a biomaterial associated infection. Presently, the time of treatment is chosen based on the assumption of being long enough to kill the infection. However, this treatment duration may not be long enough to be effective or may be a longer treatment than is necessary given the number of patient-specific variables as noted above.

The effects of electrical stimulation have been widely studied and known to be bactericidal and the total amount of treatment required to prevent or eradicate infection on a metallic surface has been shown in literature to be a driving force behind these effects. Because patients are different sizes, have different physiologic features, and inherently different intrinsic resistances, treatment is not uniform, even when voltage or current are held constant. Additionally, delivery of direct voltage does not scale linearly with implant size and current varies as a result; therefore, it is challenging to determine total treatment based on size alone.

Accordingly, there is a prevailing need in the field to provide a technique to more efficiently and reliably treat to eradicate bacteria from an implanted device.

BRIEF DESCRIPTION

According to one aspect, there is provided a method for treating a metallic surface in order to eradicate bacteria on the metallic surface, the method comprising applying a stimulation voltage to the metal surface sufficient to disrupt bacteria, measuring the accumulated charge over time, comparing the accumulated charge to a threshold level; and continuing to apply the stimulation voltage until the accumulated charge exceeds the threshold level.

According to another aspect, there is provided a system for treating an infected metallic implant, the system comprising a device capable of applying a stimulation voltage, a working electrode coupled to the device capable of applying a stimulation voltage, in which the working electrode is the metallic implant, a counter electrode, a reference electrode, each of the counter electrode and the reference electrode being coupled to the device capable of applying the stimulation voltage and forming an electrochemical circuit with the working electrode, and a processor programmed to measure accumulated charge in order to control the duration of treatment of the metallic implant.

The proposed invention is an improved method to treat patients suffering from metallic implant associated infection through charge based electrical stimulation. This can be accomplished using two, three, or four electrode systems. A preferred embodiment is a three-electrode stimulation treatment system because of its ability to provide a constant voltage through the use of a stable reference electrode. More specifically, the present invention resolves the problem of patient specific factors affecting the time under treatment by measuring charge transfer as a method of preventing or eradicating an infection on metallic surfaces. This invention requires the measure of the total charge transferred into the implant, or the integration of current drawn from the stimulation source and supplied over time. The present invention then utilizes the calculation of charge transfer to determine the amount of treatment delivered to a patient and uses this calculation as means for determining whether the implant infection has been properly cleared or prevented.

The present invention relates to the use of voltage controlled electrical treatment to metallic surfaces as a method to prevent and eradicate microbial colonization on the surface. This invention is implemented when a DC electrical current is applied to a metallic implant. As noted above, the treatment system requires at least two electrodes, but can also utilize three electrodes or four electrodes. Specifically, and according to a preferred embodiment three (3) electrodes are utilized, including a working electrode, a counter electrode, and a reference electrode. The counter electrode delivers the current to the working electrode to maintain a steady DC potential with respect to the stable reference electrode. A treatment system having two electrodes does not have a stable reference electrode and the voltage is therefore unstable.

This invention takes information about the current delivered from the counter electrode to the working electrode and calculates the charge by integrating this value over time. This allows the measured accumulated charge delivered to the system during electrical stimulation to determine the level of treatment applied, as well as the ultimate duration of treatment. The specific value for these variables required to be bactericidal is dependent on the specific conditions of treatment, surface area of the infected implant, and the pathogen of interest. Additionally, patient size, hydration, and other physiologic parameters will dictate how much resistance is present from the skin based counter electrode to the working electrode implant. As previously noted, these parameters dictate how much current is passed to the implant and ultimately how much charge is delivered in a specific amount of time. This can vary greatly between patients, making it such that, over a period of time, at the same input parameters of voltage applied, two different patients may receive different treatments. The present invention is preferred and advantageous because it normalizes treatment over each of these variables, allowing for a known charge-based treatment to be applied, regardless of stimulation input parameters, and in which time is no longer the determining factor for completing a successful treatment.

Using this invention, the exact amount of treatment can be determined through calculation of the total charge passed into the system and how much infection has been cleared as a result. This methodology normalizes eradication and prevention treatment times, accounting for differences in body resistances, current, duration, and voltage parameters. This method ensures each patient receives the same treatment. According to at least one version, a treatment system can be configured to automatically terminate treatment upon an accumulated charge transfer reaching a predetermined threshold value. In another version, the treatment system can be configured to discontinue treatment even if the accumulated charge has not reached the predetermined threshold value, but in which the treatment has exceeded a time threshold.

Charge based treatment uniquely accounts for and considers all parameters between patient anatomy and electrochemical treatment, thereby normalizing the treatment for prevention or eradication of infection on metallic surfaces to ensure every patient is treated the same. This invention is unique because it allows for the accurate calculation of total amount of charge transferred in real time, allowing for a normalized electrical stimulation treatment between patients to be achieved.

These and other features and advantages will be readily apparent from the following Detailed Description, which should be read in conjunction with the accompanying drawings.

DETAILED DESCRIPTION

The following relates to a method of treatment for eradicating bacteria from a metallic implant, such as an orthopedic or dental appliance, using a stimulation voltage in which the degree of treatment is based on accumulated charge transfer. It will be understood that various modifications are possible within the scope of the intended invention.

As previously noted, electrical stimulation for infection control on metal implants can be usually implemented in two, three, and four electrode systems, such as through the application of a cathodic stimulation voltage applied by a potentiostat or similar device to the implant in which the implant is the working electrode of the treatment system. Principles of this treatment system (CVCES) are described in U.S. Pat. No. 9,612,142, the entire contents of which are herein incorporated by reference. In a two-electrode treatment system, current is passed from the counter electrode to the working electrode and the voltage on the working electrode can vary. In this case, the current carrying electrodes are also being utilized for sense measurement. The two-electrode system measures the entire cell voltage drop across the electrochemical cell from the working electrode, through the electrolyte and to the counter electrode. A four-electrode treatment system measures impedance across a solution phase interphase, allowing for an accurate measure of solution resistance or resistance across the surface of some material. The latter treatment system does not, however, provide information about the electrochemical reactions occurring at the working or counter electrodes. While the present invention is applicable to both two and four-electrode systems, three (3) electrode treatment systems are preferred.

Figure 1:
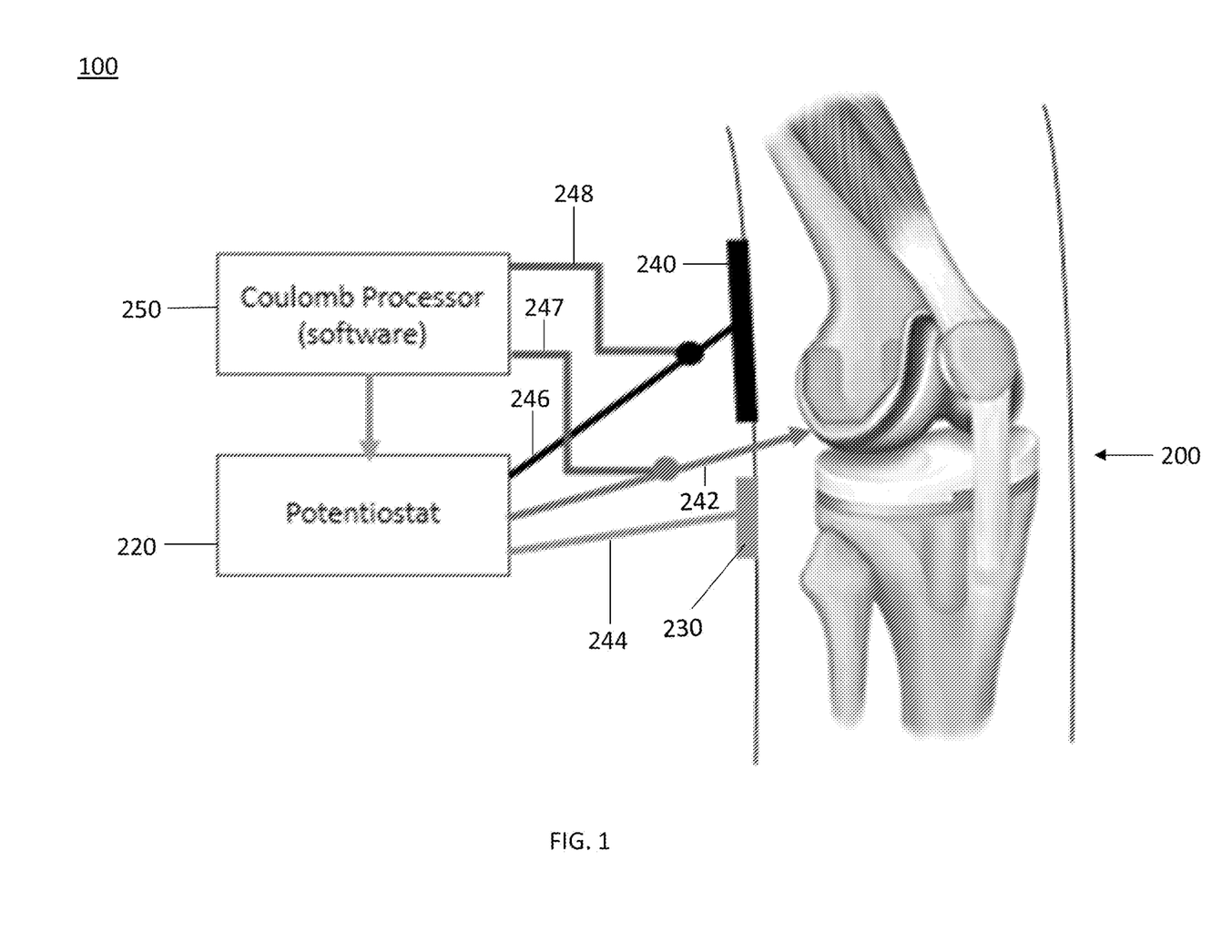
FIG. 1 is a schematic diagram of an exemplary implant treatment system employing the herein described method.

Accordingly, a three-electrode treatment system 100 for use in accordance with the present invention is shown schematically in FIG. 1 and more specifically as used in connection with a surgically implanted knee replacement (implant 200) having metallic tibial and femoral components. A potentiostat 220 is electrically coupled to the implant 200 by at least one electrical lead 242, including a needle placed in direct contact with the implant 200. A counter electrode 240 and a reference electrode 230 are also coupled to the potentiostat 220 via electrical leads 246 and 244, respectively. According to this exemplary embodiment, a processor 250 is coupled to the potentiostat 220 and further programmed with processing logic or software/firmware in which current flow between the working electrode 200 and counter electrode 240 is measured, as discussed herein via separate leads 247, 248 connected to the working electrode and counter electrode leads 242, 246, respectively.

Three-electrode setups separate the stable reference electrode 230 from the counter electrode 240, and places the reference electrode 230 in close proximity to the working electrode (e.g., the implant 200). This configuration is distinctly advantageous, when compared to a two-electrode system because it only measures the potential in half of the electrochemical cell, the working electrode, providing a clear indication of what is happening electrochemically on the surface of that implant. Additionally, compared to the four-electrode system, a three-electrode configuration is preferred because this configuration allows for the direct analysis of electrochemical reactions on the working electrode. Potential changes of the working electrode are measured independently of changes that may occur on the counter electrode. Because of this isolation, a three-electrode configuration is the preferred method of treatment in electrochemical experimentation and is the basis for the preferred embodiment of this invention.

All corrosion reactions have a cathodic half-cell reaction, an anodic half-cell reaction, an electrolyte solution and a means of electron transport between cathodic and anodic half-cell reactions. The application of electrical stimulation for infection control on metallic implants is often maintained constant in the cathodic region using three-electrode stimulation configurations. Metallic implants are often passivated metals such as titanium alloys, stainless steel, and cobalt chrome, amongst others. In the human body, soft tissue represents the means of electron transport. The cathodic half-cell reaction is represented by the oxygen and water reduction reactions and the anodic half-cell reaction consists of metal oxidation. The rate of reactions is measured by the electron flow (current). The current being delivered to the implant is influenced by the electrical input parameters, as well as external factors like patient resistance, distance between the counter electrode and working electrode, distance between counter electrode and reference electrode, resistances between electrodes, and size of the implant, among others.

The amount of current that the implant receives has a direct influence on the technology's ability to eradicate and prevent infection, with more current typically being associated with higher kill rates and efficacy. Because every patient is different, there needs to be a way to normalize electrical stimulation for infection control from patient to patient, ensuring that the expected bactericidal effect is achieved. Reduction reactions are dominant when there is a net cathodic current and oxidation reactions dominate in the presence of a net anodic current. The oxygen and water reduction reactions are represented by the following Equation 1 and Equation 2:

$$O_2 + H_2O + 4e^- \rightarrow 4OH^- \quad \text{Equation 1:}$$

$$2H_2O + 2e^- \rightarrow H_2 + 2OH^- \quad \text{Equation 2:}$$

At pH 7, like the pH in the human body, the standard reduction potential of oxygen reduction is +0.8V and the standard reduction potential of water reduction is −0.4V. At applied cathodic potentials, the oxygen reduction reaction becomes diffusion limited and water reduction becomes the dominant cathodic half-cell reaction. The potentials applied for the prevention and eradication of infection from metallic implants falls within these oxygen and water reductions regimes. As can be seen in Equation 1 and Equation 2, and through the production of OH— (hydroxide ions) in both cases, the pH is increased in the microenvironment directly surrounding the metallic implant and kills the infection. The production of OH— is dependent on the rate of the reactions, as dictated by the current (or electrons) flowing through the electrode-electrolyte interface. In the case of electrical stimulation for infection control in the human body, the resistance of the electrode-electrolyte interface varies widely between patients; therefore, even at the same applied voltage, the current delivered can vary. Because the rate of bactericidal activity is dependent on the production of OH—, and therefore the current flow, the higher the current, the more rapidly this can occur. As such, the present invention relates the products of the reaction to the charge transfer, allowing different implants to receive the same treatment from a constant voltage, all while receiving different currents because of differences in resistances. The total amount of charge transferred into the system will produce an equal number of products of the reaction.

As the current increases, so too does the production of OH— ions. This increased production therefore drives the pH in the microenvironment surrounding the implant more alkaline, and eventually to bactericidal levels. At higher levels of charge transfer, the reaction has been completed more times, resulting in this increased pH more rapidly than lower charge transfer. This consequentially leads to a more rapid bactericidal effect.

Figure 2A:
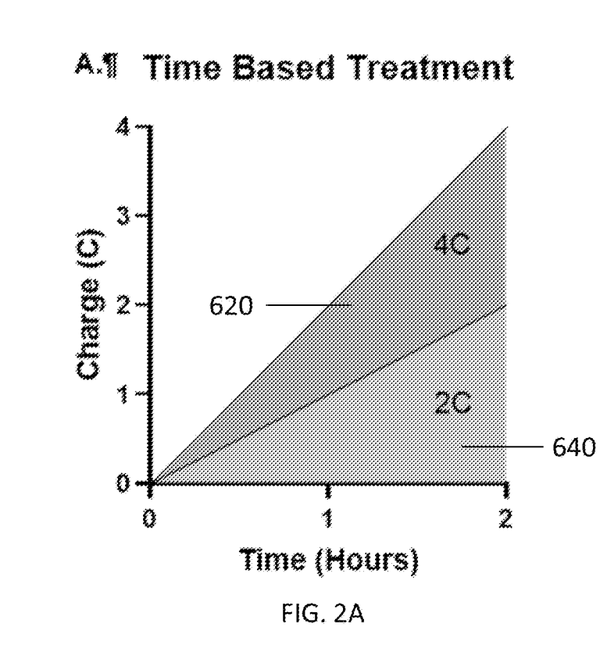
FIGS. 2A and 2B are graphical representations comparing time and charge-based treatments, respectively, between patients.
Figure 2B:
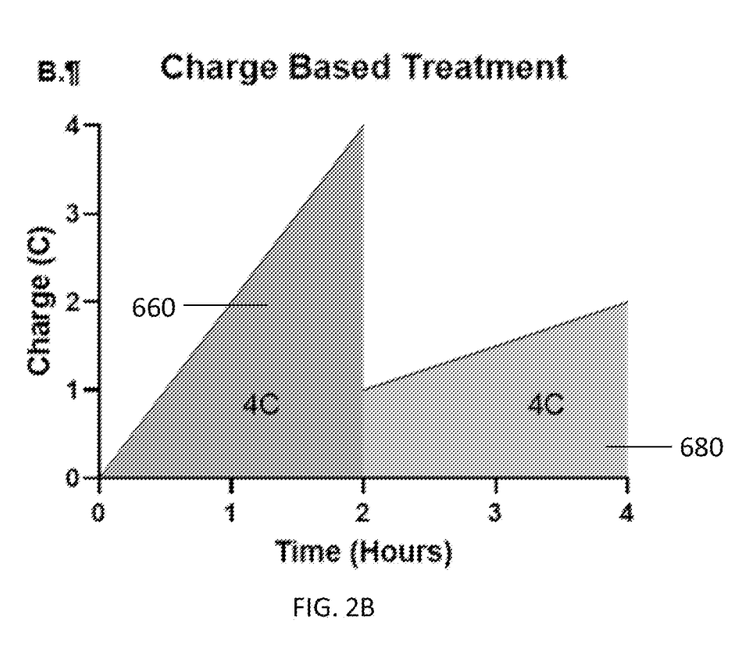

If a patient is treated solely based on time, certain patients may receive too much treatment while other patients may not receive sufficient treatment to eradicate the bacteria. Differences between time-based treatments and charge-based treatments are depicted in FIGS. 2A and 2B. FIG. 2A illustrates a fictitious example of what may typically occur in the case of a time-based stimulation voltage treatment for two different patients, namely patient A and patient B with charge in coulombs being charted relative to time of treatment (measured in hours). In this case, Patient A (plot 620) and Patient B (plot 640) are assumed to have the same treatment voltage and time. As can be seen, it is therefore possible for certain individuals to receive more, or less, treatment than necessary with Patient A receiving 4 coulombs and Patient B receiving only 2 coulombs in this illustrative example.

FIG. 2B provides a visual representation of a charge-based treatment to illustrate the inventive methodology. In this representation, the treatment considers the different rates of current delivery into different patients due to resistance and counts the accumulation of charge in the system. Then, after the designated amount of charge has been reached, the treatment is considered complete and no additional treatment is delivered. In this hypothetical example, Patient A was complete with treatment after only 2 hours per plot 660, whereas Patient B required 4 hours per plot 680. Accordingly, the foregoing FIGS. 2A and 2B provides an extreme example of why the present invention is needed in the case of electrical stimulation for infection control of metallic implants.

The present invention is directed to a method to ensure a charge-based treatment for delivery of electrical stimulation for treatment and prevention of metal associated biofilm infections. As discussed, herein the herein described method can involve any or all of the following:
1. Sampling of current every second and summing of the sampled current to give the charge transfer in real time;
2. Intermittently integrating the current over time to determine the total charge at a given time;
3. Stopping the treatment when a threshold or goal charge transfer treatment has been achieved;
4. Have the capability to display the percentage of treatment complete based on accumulated charge transfer and estimate a time until completion; and 5. Provide an override feature that allows the treatment to be shut off after a set amount of time, even if the total charge transfer has not been achieved. Each of these features will be described in detail below to further describe the technology.

For purposes of the following description, a treatment system such as treatment system 100, FIG. 1, can include the specially programmed processor 250 that is coupled to the potentiostat 220 or alternatively, the potentiostat 220 can be suitably programmed without the need for the separate device 250. The amount of electrical charge that flows into a system is designated by the current flow and how long the current flows as measured by the processor 250, the latter receiving current from the working and counter electrodes 200, 240 via connective leads 247, 248. Equation 3 illustrates the equation for calculating charge transfer:

$$Q=I*t \qquad \text{Equation 3:}$$

in which Q is the charge, measured in coulombs (C), I is the current measured in amperes (A), and t represents time measured in seconds (s). Given this information, the processor or potentiostat is programmed to measure and record the current output, in amperes, every second or other predetermined sampling interval and track a continuous summation of the current values. Based on Equation 1, this summation will provide an indication of the total charge transfer, in coulombs, delivered into the treatment system after any given period that the stimulation voltage has been delivered.

An alternative to this method utilizes Equation 4 in which the current is intermittently integrated over time in order to determine the total charge. Equation 4 states:

$$Q=\int I\, dt \qquad \text{Equation 4:}$$

This is an alternative embodiment that allows for the calculation of charge transfer through the integration of the constantly output current vs. time plot. In this case, it is not required that there be a 1 second sampling period, but instead the sampling period could be much faster or slower. While this obtains the same result as the first idea represented by Equation 1, this method is more cumbersome and is therefore an alternative embodiment.

An important distinction of this invention to the current practice is its ability to terminate treatment based on charge as opposed to time or duration. In accordance with the methodology of this invention, the delivery of electrical current to the implant 200 will be discontinued when the charge transfer reaches a specific, predetermined and set limit (an accumulated charge transfer threshold value) that is preferably stored by the potentiostat or processor 250. For purposes of this method, the summed current is compared by the processor 250, FIG. 1, following each sampling to the accumulated charge transfer threshold value. This is an important factor in the current design as opposed to known time-based treatment systems and methodology. Having a cutoff point or threshold value when the proper amount of charge has been achieved will ensure no patient is over treated, and no patient is undertreated, with the electrical stimulation for implant infection control. According to one version, the estimated percentage of completion can be calculated in software and output for the patient or caregiver to see based on how much total charge has been transferred at that moment. The system is further configured according to a preferred embodiment, with a display in which the processor 250 or the potentiostat 220 is programmed to display the percentage of treatment complete (based on the amount of charge transfer measured/summed) and estimate a time until completion, enabling patients to be aware of how much time may be remaining in their treatment.

According to another aspect, the potentiostat 220 or separate processor 250 can further can be programmed with a timer in which stimulation treatment is automatically shut off after a set amount of time, even if the total coulombic transfer threshold value has not been achieved. It is to be understood that during active treatment delivery, the patient will mainly remain immobile. This lack of mobility is essential to ensure that the applied treatment is constant, with no detachment of the electrical stimulation apparatus, and an assurance that a consistent charge is being delivered to the patient. Realistically, however, there is a limited amount of time that any patient can stay immobile. The herein described charge-based treatment delivery is not dictated upon a set time that the treatment will be applied to the implant. As such, if there is an extended treatment due to patient-related factors or due to an anomaly in the treatment system, patients will have been immobile for too long. Accordingly and according to a preferred version, the herein described treatment system includes an override feature in which the processor is programmed to turn off treatment when the total charge (threshold value) is achieved, or when a predetermined amount of time has been reached. The foregoing termination feature maintains patient safety and eliminates the possibility of patients having overly extensive treatment times.

The described invention is a significant improvement over the current treatment delivery parameters based solely on arbitrary time periods. This invention utilizes real time calculations of charge using the output of current and time in order to apply a predetermined charge level of treatment. This methodology normalizes the results across the applied voltage. Additionally, the treatment is normalized for any differences in current between the counter and working electrodes that may ensue from variations in patient weight, skin/fat composition, conductivities due to hydration, implant material, and electrode placement. Finally, and most importantly, the herein described methodology ensures that every patient is given the same treatment through patient specific treatment parameters.

Additionally, the amount of charge transfer required to treat or prevent infection is dependent on the size of the implant. Larger implants have a greater total current through the electrode/electrolyte interface. As such, the total charge transfer will increase as a function of implant size and larger implants will require more charge to reach bactericidal levels. This raises the important concept of charge density. The charge through 1 $cm^2$ of implant material will remain relatively constant across all implant sizes, while the total charge through the interface will be a function of implant size.

Figure 3:
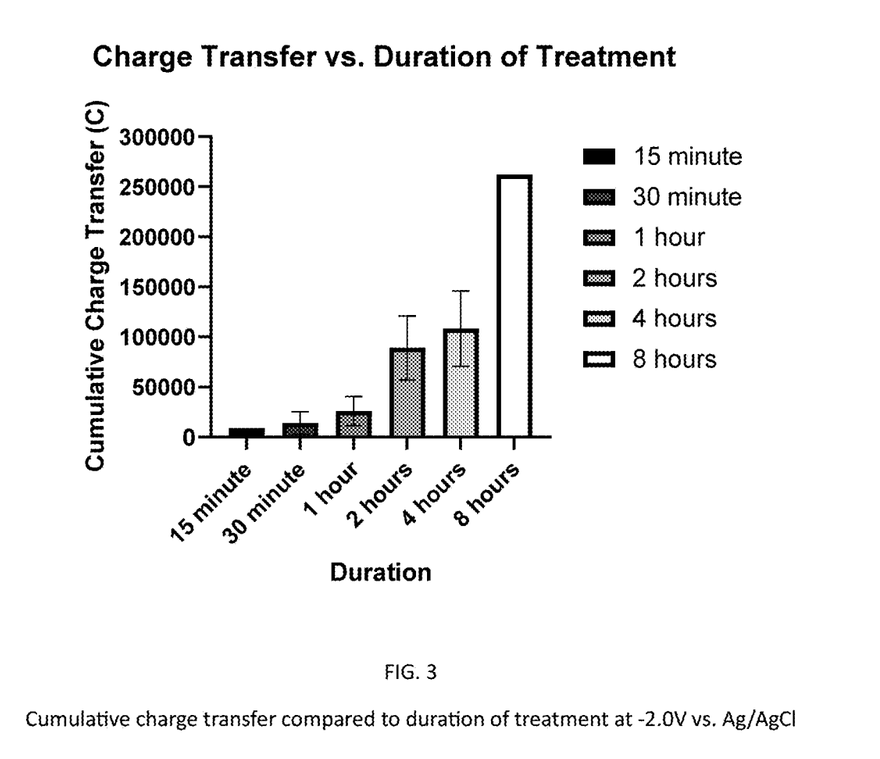
FIG. 3 is a graphical representation depicting cumulative charge transfer (in coulombs) compared to treatment duration at −2.0V vs. Ag/AgCl.

The foregoing concepts and methodology have been shown to be valid in testing. FIG. 3 represents data collected during testing that empirically shows Equation 4, in which a longer treatment time resulting in higher amounts of charge being transferred when treated with the same treatment voltage, which is shown for a cumulative charge transfer (coulombs) taken periodically over time and extending to eight (8) hours duration.

Figure 4:
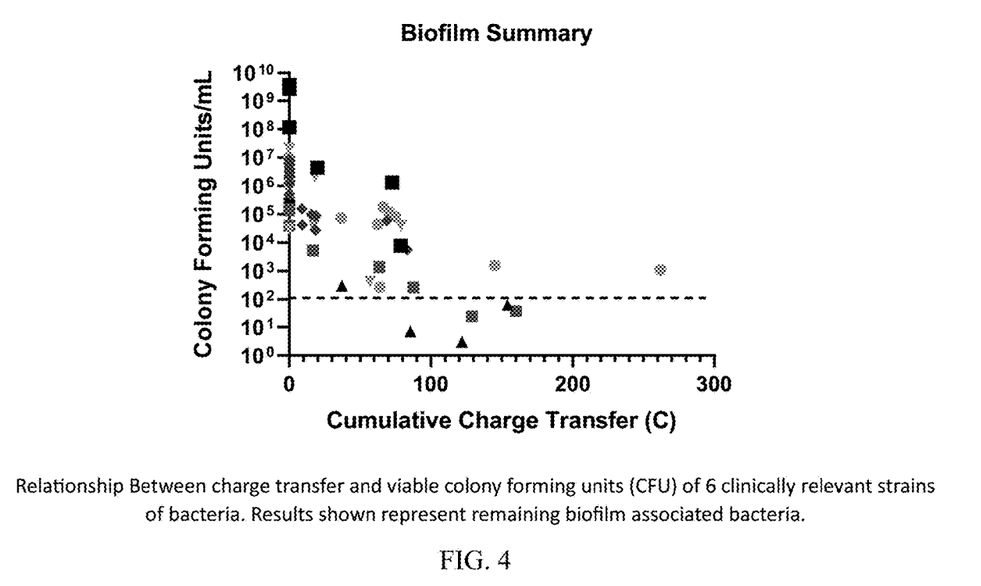
FIG. 4 is a graphical representation depicting the relationship between charge transfer and viable colony forming units (CFU) of six (6) clinically relevant strains of bacteria with the results shown being remaining biofilm associated bacteria.
Figure 5:
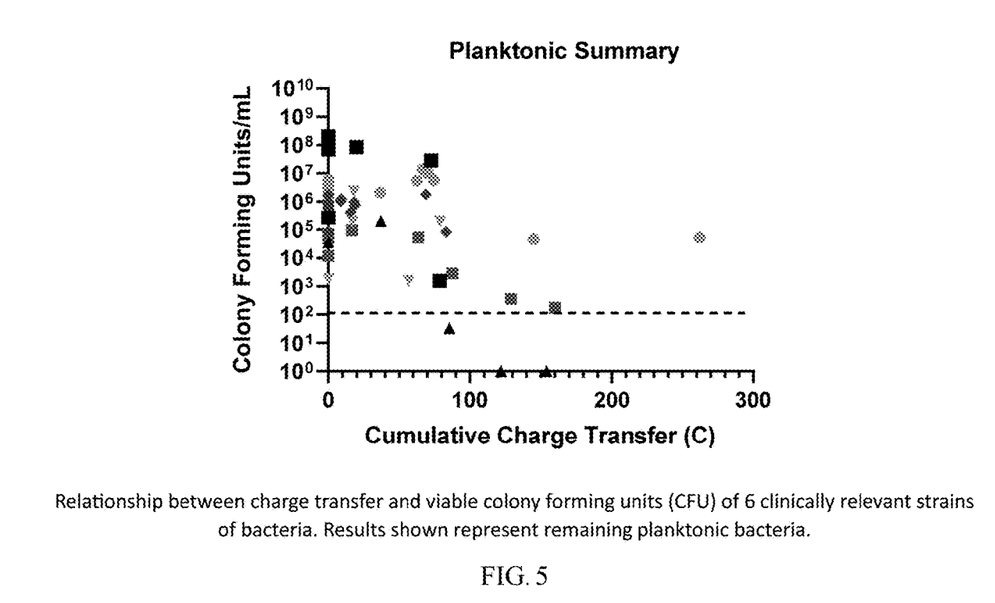
FIG. 5 is a graphical representation showing the relationship between charge transfer and viable colony forming units (CFU) of the six (6) clinically relevant strains of bacteria of FIG. 4, in which the results shown represent remaining planktonic bacteria.

FIGS. 4 and 5 illustrate a distinct inverse relationship between viable colony forming units (CFU) and cumulative charge transferred into the system during treatment for eradication of a preformed biofilm structure, when all durations from FIG. 2 are compared based upon cumulative charge transfer. More specifically, FIG. 4 represents the results taken with increased charge transfer after different levels of treatment and involving biofilm associated bacteria from six (6) different clinically relevant strains. FIG. 5 represents data collected in testing that shows the same relationship for viable planktonic, free-floating, CFU and cumulative charge for the same six (6) clinically relevant strains according to FIG. 4. In each instance, the more charge that is transferred into the system, the greater the reduction in viability.

One challenge that arose while creating this invention included understanding the value of charge transfer and how this parameter relates to killing bacteria. This challenge was addressed through significant experimentation with a variety of pathogens and material types as shown in FIGS. 3-5. This experimentation allowed enabled a determination of the minimum amount of charge required to kill a variety of gram-positive and gram-negative pathogens. An additional challenge was in providing a way to uniformly compare data when there were differences in voltage, current, or duration. According to the present invention and using charge transfer, it is possible to calculate the amount of time a patient treatment needs to run, at a certain voltage or current level, for its effects to be bactericidal. This technique normalizes data, from a variety of different treatment parameters, that was not otherwise comparable. As a result, the overall methodology of the present invention improves patient treatment outcomes, as well as the consistency of treatment delivery between patients.

PARTS LIST FOR FIGS. 1-5

100 treatment system
200 implant (working electrode)
220 potentiostat
230 reference electrode
240 counter electrode
242 electrical lead
244 electrical lead
246 electrical lead
247 lead
248 lead
250 processor
620 plot
640 plot
660 plot
680 plot It will be readily apparent that other modifications and/or variations are possible within the intended ambits of the invention, and in accordance with the following claims.

The invention claimed is:

1. A method for treating a metallic surface of an implantable device in order to eradicate infectious bacteria, the method comprising:
   a) enabling a stimulation device of a treatment system capable of applying a DC voltage sufficient to disrupt the bacteria from the metallic surface of the implantable device, the DC voltage being applied between a pair of electrodes, and in which one of the electrodes is the implantable device;
   b) using a processor of the treatment system, measuring an accumulated charge transfer to the metallic surface of the implantable device over time, the accumulated charge transfer being measured in coulombs;
   c) comparing the measured accumulated charge transfer to a predetermined charge transfer threshold level stored by the processor; and
   d) continuing to apply the DC voltage until the measured accumulated charge transfer exceeds the predetermined charge transfer threshold level.

2. The method according to claim 1, in which the accumulated charge transfer is measured by sampling current between the pair of electrodes over periodic time intervals and then summing the sampled current.

3. The method according to claim 1, in which the accumulated charge transfer is measured by integrating current between the pair of electrodes over a specific time interval.

4. The method according to claim 1, further comprising: continuing to apply the DC voltage until the accumulated charge transfer exceeds the predetermined charge transfer threshold level or following a predetermined maximum time period measured from the start of treatment, whichever occurs first.

5. The method according to claim 1, further comprising: displaying a percentage amount of treatment completed, based on the measured accumulated charge transfer.

6. The method according to claim 1, wherein the metallic surface is made from at least one of stainless steel, cobalt-chromium, and titanium.

7. The method according to claim 1, wherein the metallic surface is that of a surgical implantable device.

8. The method according to claim 1, further comprising coupling the metallic surface to a potentiostat capable of applying the DC voltage.

9. The method according to claim 8, further comprising coupling the metallic surface to a reference electrode and a counter electrode, each being coupled to the potentiostat and forming a circuit, wherein the metallic surface acts as a working electrode of the treatment system.

10. A system for treating an infected metallic implant, the system comprising:
    a device capable of applying a stimulation DC voltage capable of disrupting bacteria;
    a working electrode coupled to the device capable of applying the stimulation DC voltage, in which the working electrode is the metallic implant;
    a counter electrode;
    a reference electrode, each of the counter electrode and the reference electrode being coupled to the device capable of applying the stimulation DC voltage and forming an electrochemical circuit with the working electrode; and
    a processor programmed to measure an accumulated charge transfer to the metallic implant over time in order to control the duration of treatment of the metallic implant, wherein the processor is programmed to compare the accumulated charge transfer to the metallic implant, measured in coulombs, to a predetermined charge transfer threshold level stored by the processor and terminate treatment when the accumulated charge transfer meets or exceeds the predetermined charge transfer threshold level.

11. The system according to claim 10, in which the processor is further programmed to terminate treatment when the accumulated charge transfer exceeds the predetermined charge transfer threshold value or if the total time of treatment exceeds a stored maximum treatment period, whichever occurs first.

12. The system according to claim 10, wherein the processor is further programmed to display an extent of the treatment based on a percentage of measured accumulated charge transfer as compared to the predetermined charge transfer threshold value.

13. The system according to claim 10, in which the processor is configured to sample current at the working electrode at periodic time intervals and sum the sampled current in order to measure the accumulated charge transfer.

14. The system according to claim 10, in which the processor is configured to measure current over a predetermined time interval and then to integrate the measured current over the predetermined time interval in order to measure the accumulated charge transfer.

15. The system according to claim 10, in which the processor is disposed within the device capable of applying the stimulation DC voltage.

16. The system according to claim 10, wherein the metallic implant is made of at least one of stainless steel, cobalt-chromium, and titanium.

* * * * *